United States Patent

Baird et al.

[11] 4,111,956
[45] Sep. 5, 1978

[54] PROCESS FOR THE MANUFACTURE OF HETEROCYCLIC COMPOUNDS

[75] Inventors: David Boyd Baird; James Stanley Campbell; Brian Ribbons Fishwick; Robert David McClelland, all of Manchester, England

[73] Assignee: Imperial Chemical Industries Limited, London, England

[21] Appl. No.: 764,457

[22] Filed: Jan. 31, 1977

Related U.S. Application Data

[63] Continuation-in-part of Ser. No. 630,897, Nov. 11, 1975, abandoned.

[51] Int. Cl.$^2$ ............................................. C07D 333/36
[52] U.S. Cl. ............................................. 260/329 AM
[58] Field of Search ..................... 260/329 AM, 329 R Primary Examiner—Cecilia M. Jaisle
Attorney, Agent, or Firm—Cushman, Darby & Cushman

[57] ABSTRACT

Process for manufacture of the heterocyclic compounds of the formula:

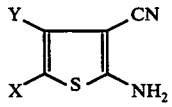

wherein
X is cyano, acyl, alkylsulphonyl, arylsulphonyl, optionally substituted alkoxycarbonyl, nitro, phenyl or sulphamoyl, and
Y is hydrogen, optionally substituted alkyl or optionally substituted aryl, which comprises reacting a compound of the formula:

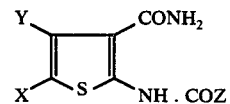

with an acid halide in the presence of a compound of the formula

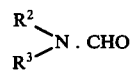

and optionally in the presence of an aprotic solvent, and subjecting the resulting compound of the formula:

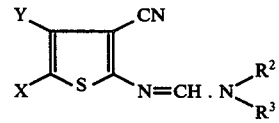

or an acid salt thereof, to hydrolysis in acidic medium, wherein Z is hydrogen or an optionally substituted alkyl or aryl radical, and $R^2$ and $R^3$ each independently representing optionally substituted alkyl, cycloalkyl or aryl radicals, or $R^2$ and $R^3$ together form with the nitrogen atom a 5- or 6-membered nitrogen-containing heterocyclic ring.

3 Claims, No Drawings

PROCESS FOR THE MANUFACTURE OF HETEROCYCLIC COMPOUNDS

This application is a continuation-in-part of application Ser. No. 630,897 filed Nov. 11, 1975, now abandoned.

This invention relates to a process for the manufacture of 2-amino-3-cyanothiophenes.

According to the invention there is provided a process for the manufacture of the heterocyclic compounds of the formula:

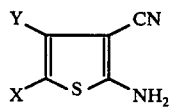

wherein

X is cyano, acyl, alkylsulphonyl, arylsulphonyl, optionally substituted alkoxycarbonyl, nitro, phenyl or sulphamoyl, and Y is hydrogen, optionally substituted alkyl or optionally substituted aryl, which comprises reacting a compound of the formula:

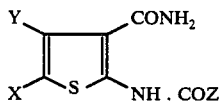 Formula I with an acid halide in the presence of a compound of the formula

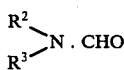

and optionally in the presence of an aprotic solvent, and subjecting the resulting compound of the formula:

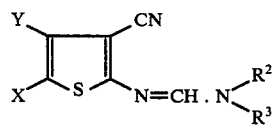

or an acid salt thereof, to hydrolysis in acidic medium, wherein Z is hydrogen or an optionally substituted alkyl or aryl radical, and $R^2$ and $R^3$ each independently representing optionally substituted alkyl, cycloalkyl or aryl radicals, or $R^2$ and $R^3$ together form with the nitrogen atom a 5- or 6-membered nitrogen-containing heterocyclic ring.

The process of the invention can be conveniently carried out by stirring the compound of Formula I and the acid halide together in the presence of the compound of the formula

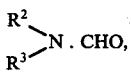

an excess of this latter compound being used as solvent for the reaction optionally in admixture with an aprotic solvent the reaction preferably being carried out at a temperature between 15° and 120° C. especially at 40° C. to 80° C., for a time up to 48 hours. The product of this stage, which may be in the form of an acid salt, may then be isolated, for example by pouring the reaction mixture into water and filtering off the precipitated solid. The hydrolysis of the resulting compound is then conveniently effected for example by stirring the compound in aqueous or alcoholic medium containing a strong inorganic or organic acid, the hydrolysis preferably being effected at elevated temperatures up to the boiling point of the reaction medium. The resulting 2-amino-3-cyanothiophene is then isolated in conventional manner, for example by diluting the mixture with water, and filtering off the precipitated solid.

The acid halides which are used in the above process are preferably phosphorus oxychloride or thionyl chloride.

The optionally substituted alkyl radicals represented by $R^2$ and $R^3$ are preferably optionally substituted lower alkyl radicals such as methyl, ethyl, propyl and butyl, and chloro lower alkyl such as β-chloroethyl. The optionally substituted aryl radicals represented by $R^2$ and $R^3$ are preferably optionally substituted monocyclic radicals such as phenyl, tolyl, xylyl, chlorophenyl and nitrophenyl. As examples of 5- and 6-membered nitrogen containing heterocyclic rings represented by $R^2$, $R^3$ and the nitrogen atom there may be mentioned pyrrolidyl, morpholinyl and piperidyl. It is however preferred that $R^2$ and $R^3$ are both lower alkyl or together form with the nitrogen atom N a 5- or 6 -membered nitrogen-containing heterocyclic ring. Above all $R^2$ and $R^3$ are both methyl. Thus the preferred compound of the formula

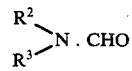

for use in the process is dimethylformamide.

As examples of the aprotic solvents which may be used in the process there may be mentioned sulpholane, dioxan, tetrahydrofuran, toluene and chlorobenzene.

As examples of strong inorganic or organic acids which can be used to effect the hydrolysis there may be mentioned hydrochloric acid, sulphuric acid, phosphoric acid and p-toluenesulphonic acid.

Throughout this specification the terms "lower alkyl" and "lower alkoxy" are used to denote alkyl and alkoxy radicals respectively containing from 1 to 4 carbon atoms.

The optionally substituted alkyl radicals represented by Z and Y are preferably optionally substituted lower alkyl radicals such as methyl, ethyl, propyl and butyl, and chloro lower alkyl such as β-chloroethyl. The optionally substituted aryl radicals represented by Z and Y are preferably optionally substituted monocyclic aryl radicals such as phenyl, tolyl, xylyl, chlorophenyl, bromophenyl or nitrophenyl. It is however preferred that Z is phenyl, lower alkyl and, above all, hydrogen.

It is also preferred that Y is hydrogen or a lower alkyl radical.

The acyl radicals represented by X are preferably lower alkyl carbonyl radicals such as acetyl, propionyl or butyryl radicals, or monocyclic aryl carbonyl radicals such as benzoyl. The alkylsulphonyl radicals represented by X are preferably lower alkylsulphonyl radicals such as methylsulphonyl, ethylsulphonyl, propylsulphonyl and butylsulphonyl. The arylsulphonyl radicals represented by X are preferably monocyclic aryl sulphonyl radicals such as benzenesulphonyl and p- toluenesulphonyl. The optionally substituted alkoxycarbonyl radicals represented by X are preferably optionally substituted lower alkoxycarbonyl radicals such as methoxycarbonyl, ethoxycarbonyl and butoxycarbonyl radicals. Preferably X is cyano or nitro.

The compounds of Formula I can be obtained, for example, by the methods which are described in Chemische Berichte 1966, 99, 95 and 1965, 98, 3571. Thus, for example, compounds wherein X is a nitro group can be obtained by nitration of the corresponding compounds wherein X is hydrogen, and compounds wherein X is alkylsulphonyl, arylsulphonyl or sulphamoyl can be obtained by appropriately treating the corresponding compounds wherein X is chlorosulphonyl.

As specific examples of the said compounds of Formula I there may be mentioned 2-formylamino-3-carbamoyl-5-nitrothiophene, 2-benzoylamino-3-carbamoyl-5-nitrothiophene, 2-formylamino-3-carbamoyl-5-(nitro-, cyano-, methoxycarbonyl-, methylsulphonyl- or acetyl-) thiophene, 2-acetylamino-3-carbamoyl 4-methyl-5-nitrothiophene and 2-acetylamino-3-carbamoyl-5-nitrothiophene.

A preferred class of the said compounds of Formula I for use in the process of the invention comprises the compounds of the formula:

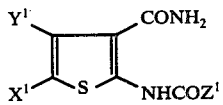

wherein $Z^1$ is phenyl or preferably hydrogen, $Y^1$ is lower alkyl, such as methyl, or preferably hydrogen, and $X^1$ is cyano or preferably nitro.

The heterocyclic compounds obtained by the process of the invention are valuable as diazo components in the production of azo dyestuffs and in particular in the production of disperse monoazo dyestuffs for synthetic textile materials.

The invention is illustrated but not limited by the following Examples in which the parts and percentages are by weight.

EXAMPLE 1

A mixture of 83.9 of 2-formylamino-3-carbamoyl-5-nitrothiophene, and 550 parts of dimethylformamide is stirred at 20° C., and 107 parts of phosphorous oxychloride is slowly added over 15 minutes, the temperature of the mixture rising spontaneously to 50° C.–55° C. The mixture is stirred for 10 minutes, the temperature gradually raised to 70°–75° C., and the mixture stirred for 3½ hours at this temperature. The mixture is then cooled, poured into 4000 parts of ice/water, and the precipitated solid filtered off, washed with water and dried.

78.4 parts of this solid, 600 parts of ethanol, 130 parts of β-methoxyethanol, 70 parts of water and 35 parts of a concentrated aqueous solution of hydrochloric acid are stirred at the boil for 3 hours. 2 parts of activated carbon are added, the mixture filtered, and the filtrate mixed with 4000 parts of water. The precipitated 2-amino-3-cyano-5-nitrothiophene is then filtered off, washed with water and dried. The overall yield is 67%.

The 2-formylamino-3-carbamoyl-5-nitrothiophene used in the above example was itself obtained as described in Belgian Pat. No. 794,418.

EXAMPLE 2

In place of the 107 parts of phosphorous oxychloride used in Example 1 there are used 83 parts of thionyl chloride whereby 2-amino-3-cyano-5-nitrothiophene is obtained in an overall yield of 59%.

EXAMPLE 3

In place of the 83.9 parts of 2-formylamino-3-carbamoyl-5-nitrothiophene used in Example 1 there are used 113.6 parts of 2-benzoylamino-3-carbamoyl-5-nitrothiophene, the first stage of the reaction being carried out for 15 minutes at 60° C. (instead of at 70°–75° C. as in Example 1). 2-Amino-3-cyano-5-nitrothiophene is obtained in an overall yield of 60%.

The 2-benzoylamino-3-carbamoyl-5-nitrothiophene was itself obtained by reacting 2-amino-3-carbamoyl thiophene with benzoyl chloride in pyridine, and nitrating the resulting compound in sulphuric acid medium at 0° C.

EXAMPLE 4

107 parts of phosphorous oxychloride are added over 15 minutes to a mixture of 83.9 parts of 2-formylamino-3-carbamoyl-5-nitrothiophene and 550 parts of N-formylpiperidine at 20° C., the temperature of the mixture rising spontaneously to 50°–55° C. The mixture is stirred for a further hour at this temperature, and is then poured into 4000 parts of ice/water. The precipitated solid is filtered off, washed with water and dried.

94.7 parts of the solid, 600 parts of ethanol, 130 parts of β-methoxyethanol, 70 parts of water and 35 parts of a concentrated aqueous solution of hydrochloric acid are stirred at the boil under a reflux condenser for 16 hours. The mixture is filtered, the filtrate diluted with 4000 parts of water, and the precipitated 2-amino-3-cyano-5-nitrothiophene filtered off, washed with water, and dried.

EXAMPLE 5

The process of Example 1 is repeated except that 100 parts of the dimethylformamide are replaced by 100 parts of tetrahydrofuran or by 100 parts of toluene, the reaction in the first stage being carried out for 24 hours at 70° to 75° C. (instead of for 3½ hours at the same temperature). Similar results are obtained.

EXAMPLE 6

107 parts of phosphorous oxychloride are added over 15 minutes to a mixture of 81.6 parts of 2-formylamino-3-carbamoyl-4-methyl-5-cyanothiophene and 550 parts of dimethylformamide at 20° C., the temperature of the mixture rising spontaneously to 50° C. The temperature is then raised to 60° C., and maintained for 15 minutes. The mixture is then cooled, poured into 4000 parts of ice/water, and the precipitated solid filtered off, washed with water and dried.

76.5 parts of this solid are then hydrolysed by the method described in the second paragraph of Example 4. 2-Amino-3:5-dicyano-4-methyl-thiophene (m.p. 206°–208° C.) is obtained in an overall yield of 52%.

The 2-formylamino-3-carbamoyl-4-methyl-5-cyanothiophene was itself obtained by formylation of 2-amino-3-carbamoyl-4-methyl-5-cyanothiophene, the preparation of which is described in German patent application No. 2,359,008 as laid open to public inspection.

EXAMPLE 7

107 Parts of phosphorous oxychloride are added over 15 minutes to a mixture of 113.6 parts of 2-formylamino-3-carbamoyl-4-phenyl-5-nitrothiophene and 550 parts of dimethylformamide at 20° C., the temperature of the mixture rising spontaneously to 55°–60° C., and this temperature is then maintained for 15 minutes. The mixture is then cooled, poured into 4000 parts of ice/water, and the precipitated solid filtered off, washed with water and dried.

93.3 parts of this solid are then hydrolysed by the method described in the second paragraph of Example 4. 2-Amino-3-cyano-4-phenyl-5-nitrothiophene is obtained.

The 2-formylamino-3-carbamoyl-4-phenyl-5-nitrothiophene was itself obtained by formylation of 2-amino-3-carbamoyl-4-phenylthiophene (Chem. Ber. 1965, Vol. 98, page 3571), which was then nitrated in sulphuric acid medium at 0° C.

EXAMPLE 8

107 parts of phosphorous oxychloride are added over 15 minutes to a mixture of 96.8 parts of 2-formylamino-3-carbamoyl-4-methyl-5-phenylthiophene and 550 parts of dimethylformamide at 20° C., the temperature rising spontaneously to 50°–55° C. After stirring for 10 minutes, the temperature is raised to 70° to 75° C. and maintained for 3 hours. The mixture is then cooled, poured into 4000 parts of ice/water, and the precipitated solid is filtered off, washed with water and dried.

86.8 parts of this solid are then hydrolysed as described in the second paragraph of Example 4 except that the reaction time is reduced to 2 hours. 2-Amino-3-cyano-4-methyl-5-phenylthiophene is obtained.

The 2-formylamino-3-carbamoyl-4-methyl-5-phenylthiophene was obtained by formylation of the corresponding 2-amino compound using a mixture of formic acid and acetic anhydride.

EXAMPLE 9

107 parts of phosphorous oxychloride are added over 15 minutes to a mixture of 89.4 parts of 2-acetylamino-3-carbamoyl-5-nitrothiophene and 550 parts of dimethylformamide at 20° C., the temperature rising spontaneously to 45°–50° C. The mixture is then cooled to 40° C., and this temperature maintained for 48 hours. The mixture is then cooled, poured into 4000 parts ice/water and the precipitated solid filtered off, washed with water, and dried.

78.4 parts of this solid are then hydrolysed by the method described in the second paragraph of Example 1. 2-Amino-3-cyano-5-nitrothiophene is obtained.

EXAMPLE 10

107 parts of phosphorous oxychloride are added over 15 minutes to a mixture of 96.0 parts of 2-formylamino-3-carbamoyl-5-phenylthiophene and 500 parts of dimethylformamide at 20° C., the temperature rising spontaneously to 55°–60° C. After stirring for 10 minutes the temperature is raised to 70°–75° C. and maintained for 6 hours. The mixture is then cooled, poured into 4000 parts of ice/water, and the precipitated solid is filtered off, washed with water and dried.

89.4 parts of this solid are then hydrolysed by the method described in the second paragraph of Example 1. 2-amino-3-cyano-5-phenylthiophene is obtained.

EXAMPLE 11

The procedure described in Example 1 is repeated except that the quantity of dimethyl formamide used is reduced to 146 parts. A similar result is obtained.

EXAMPLE 12

The procedure described in Example 1 is repeated except that the quantity of dimethylformamide used is increased to 1000 parts, and that after the reaction of the 2-formylamino-3-carbamoyl-5-nitrothiophene with phosphorus oxychloride is completed, the mixture is poured into 6000 parts of ice/water instead of the 4000 parts used in Example 1. A similar result is obtained.

EXAMPLE 13

A mixture of 83.9 parts of 2-formylamino-3carbamoyl-5-nitrothiophene and 550 parts of dimethylformamide is stirred at 20° C., and 83 parts of thionyl chloride are slowly added over 15 minutes, the temperature of the mixture rising spontaneously to 50°–55° C. The mixture is stirred for 10 minutes, the temperature is gradually raised to 70°–75° C., and the mixture is stirred for 3½ hours at this temperature. The mixture is then cooled, poured into 4000 parts of ice/water and the precipitated solid is filtered off, washed with water and dried.

78.4 parts of this solid, 600 parts of ethanol, 130 parts of β-methoxyethanol, 70 parts of water and 30 parts of concentrated sulphuric acid are stirred at the boil for 3 hours. 2 parts of activated carbon are added, the mixture is filtered, and the filtrate is mixed with 4000 parts of water. The precipitated 2-amino-3-cyano-5-nitrothiophene is then filtered off, washed with water and dried. The overall yield is 62%.

EXAMPLE 14

107 parts of phosphorus oxychloride are added over 15 minutes to a mixture of 81.6 parts of 2-formylamino-3-carbamoyl-4-methyl-5-cyanothiophene and 550 parts of dimethylformamide at 20° C., the temperature of the mixture rising spontaneously to 50° C. The temperature is then raised to 60° C., and maintained at this level for 15 minutes. The mixture is then cooled, poured into 4000 parts of ice/water, and the precipitated solid is filtered off, washed with water and dried.

76.5 parts of this solid, 600 parts of n-propanol, 180 parts of water and 35 parts of a concentrated aqueous solution of hydrochloric acid are stirred at the boil for 3 hours. 2 parts of activated carbon are added, the mixture is filtered and the filtrate is mixed with 4000 parts of water. The precipitated 2-amino-3,5-dicyano-4-methylthiophene is then filtered off, washed with water and dried. The overall yield is 51%.

EXAMPLE 15

107 parts of phosphorus oxychloride are added over 15 minutes to a mixture of 81.6 parts of 2-formylamino-3-carbamoyl-4-methyl-5-cyanothiophene and 550 parts of dimethylformamide at 20° C., the temperature of the mixture rising spontaneously to 50° C. The temperature is then raised to 60° C., and maintained at this level for 15 minutes. The mixture is then cooled, poured into 4000 parts of ice/water, and the precipitated solid is filtered off, washed with water and dried.

76.5 parts of this solid, 1000 parts of β-ethoxyethanol and 40 parts of a concentrated aqueous solution of hydrochloric acid are stirred at 25° C. for 72 hours. The mixture is then poured into 2000 parts of water and stirred for 15 minutes. The precipitated 2-amino-3:5-dicyano-4-methylthiophene is filtered, washed with water and dried.

EXAMPLE 16

The procedure described in Example 1 is repeated except that the quantity of phosphorus oxychloride is increased to 178 parts. A similar result is obtained.

EXAMPLE 17

The procedure described in Example 1 is repeated except that the quantity of phosphorus oxychloride is reduced to 60 parts. A similar result is obtained.

We claim:
1. Process for the manufacture of the thiophene compounds of the formula:

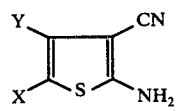

wherein
Y is selected from the class consisting of hydrogen, lower alkyl and phenyl; and
X is selected from the class consisting of nitro, cyano and phenyl, which comprises reacting a compound of the formula:

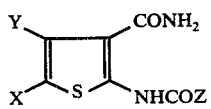   Formula I wherein Y and X have the meanings stated and Z is selected from the class consisting of hydrogen, lower alkyl and phenyl, with from 1 to 3 moles per mol of the compound of the formula I of an acid halide selected from the class consisting of phosphorus oxychloride and thionyl chloride in the presence of from 5 to 35 moles per mol of the compound of formula I of a compound of the formula:

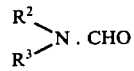

wherein $R^2$ and $R^3$ are each lower alkyl or $R^2$ and $R^3$ together form with the nitrogen atoms a 5- or 6-membered nitrogen-containing hetercyclic ring, said reaction being carried out at a temperature from 40° to 80° C., and subjecting the resulting compound to hydrolysis by heating it in a medium comprising water, at least one alcohol selected from the class consisting of ethanol, β-methoxyethanol, β-ethoxyethanol and n-propanol and an acid selected from the class consisting of hydrochloric acid and sulphuric acid.

2. Process as claimed in claim 1 wherein the compound of the formula:

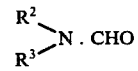

is dimethylformamide.

3. Process as claimed in claim 1 wherein the compound of the formula

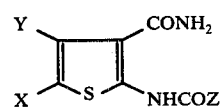

is 2-formylamino-3-carbamoyl-5-nitrothiophene.

* * * * *

UNITED STATES PATENT AND TRADEMARK OFFICE
CERTIFICATE OF CORRECTION

PATENT NO. : 4,111,956

DATED : September 5, 1978

INVENTOR(S) : David Boyd Baird; James Stanley Campbell; Brian Ribbons Fishwick; Robert David McClelland It is certified that error appears in the above-identified patent and that said Letters Patent are hereby corrected as shown below:

In the heading of the patent, add:

--[30]  Foreign Application Priority Data

December 5, 1974    Great Britain .... 52623/74--

<u>Column 3</u>, line 50, the word "parts" should be inserted after "83.9"

line 51, the comma should be deleted line 53, "is" should be changed to --are--

Signed and Sealed this

Fifth Day of June 1979

[SEAL]

Attest:

RUTH C. MASON
*Attesting Officer*

DONALD W. BANNER
*Commissioner of Patents and Trademarks*